United States Patent
Yorkston et al.

(10) Patent No.: US 9,597,044 B2
(45) Date of Patent: *Mar. 21, 2017

(54) EXTREMITY IMAGING APPARATUS FOR CONE BEAM COMPUTED TOMOGRAPHY

(71) Applicant: Carestream Health, Inc., Rochester, NY (US)

(72) Inventors: John Yorkston, Penfield, NY (US); Robert J. Asento, Rochester, NY (US); Jeffrey H. Siewerdsen, Baltimore, MD (US); David H. Foos, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/012,995

(22) Filed: Feb. 2, 2016

(65) Prior Publication Data

US 2016/0151029 A1 Jun. 2, 2016

Related U.S. Application Data

(63) Continuation of application No. 14/639,363, filed on Mar. 5, 2015, now Pat. No. 9,277,899, which is a (Continued)

(51) Int. Cl.
*A61B 6/03* (2006.01)
*A61B 6/00* (2006.01)
*A61B 6/04* (2006.01)

(52) U.S. Cl.
CPC ............. *A61B 6/4085* (2013.01); *A61B 6/03* (2013.01); *A61B 6/032* (2013.01); *A61B 6/035* (2013.01);
(Continued)

(58) Field of Classification Search
CPC ....... A61B 6/032; A61B 6/035; A61B 6/5205; A61B 6/4085
See application file for complete search history.

(56) References Cited

U.S. PATENT DOCUMENTS 4,316,091 A 2/1982 Bernardi
4,741,015 A 4/1988 Charrier
(Continued)

FOREIGN PATENT DOCUMENTS

CN 1617688 5/2005
DE 198 46 980 10/1999
(Continued)

OTHER PUBLICATIONS

International Search Report mailed Nov. 22, 2010 for International Application No. PCT/US2010/001308, 2 pages.
(Continued)

*Primary Examiner* — Hoon Song

(57) ABSTRACT

An apparatus for cone beam computed tomography of an extremity has a digital radiation detector and a first device to move the detector along a circular detector path extending so that the detector moves both at least partially around a first extremity of the patient and between the first extremity and a second, adjacent extremity. The detector path has radius R1 sufficient to position the extremity approximately centered in the detector path. There is a radiation source with a second device to move the source along a concentric circular source path having a radius R2 greater than radius R1, radius R2 sufficiently long to allow adequate radiation exposure of the first extremity for an image capture by the detector. A first circumferential gap in the source path allows the second extremity to be positioned in the first circumferential gap during image capture.

19 Claims, 20 Drawing Sheets

Related U.S. Application Data continuation of application No. 14/266,861, filed on May 1, 2014, now Pat. No. 8,998,486, which is a continuation of application No. 13/681,579, filed on Nov. 20, 2012, now Pat. No. 8,746,972, which is a continuation of application No. 12/771,250, filed on Apr. 30, 2010, now Pat. No. 8,348,506.

(60) Provisional application No. 61/175,091, filed on May 4, 2009.

(52) U.S. Cl.
CPC .............. *A61B 6/04* (2013.01); *A61B 6/4441* (2013.01); *A61B 6/4452* (2013.01); *A61B 6/466* (2013.01); *A61B 6/505* (2013.01)

(56) References Cited

U.S. PATENT DOCUMENTS

| | | | |
|---|---|---|---|
| 5,014,293 A * | 5/1991 | Boyd | A61B 6/4441 378/11 |
| 5,748,704 A | 5/1998 | Mazess et al. | |
| 6,131,690 A | 10/2000 | Galando et al. | |
| 6,236,704 B1 | 5/2001 | Navab et al. | |
| 6,580,777 B1 | 6/2003 | Ueki et al. | |
| 6,940,941 B2 | 9/2005 | Gregerson et al. | |
| 7,001,045 B2 | 2/2006 | Gregerson et al. | |
| 7,108,421 B2 | 9/2006 | Gregerson et al. | |
| 7,224,764 B2 | 5/2007 | Sukovic et al. | |
| 7,388,894 B2 | 6/2008 | O'Daniel et al. | |
| 7,388,941 B2 | 6/2008 | Sukovic et al. | |
| 7,394,888 B2 | 7/2008 | Sukovic et al. | |
| 7,460,636 B2 | 12/2008 | Ein-Gal | |
| 8,210,745 B2 | 7/2012 | Yorkston et al. | |
| 8,348,506 B2 | 1/2013 | Yorkston et al. | |
| 9,240,045 B2 | 1/2016 | Noshi et al. | |
| 2004/0022350 A1* | 2/2004 | Gregerson | A61B 6/032 378/15 |
| 2004/0096035 A1 | 5/2004 | Yamazaki et al. | |
| 2005/0053185 A1 | 3/2005 | Sukovic et al. | |
| 2005/0053186 A1 | 3/2005 | Sukovic et al. | |
| 2006/0245539 A1 | 11/2006 | Sukovic et al. | |
| 2008/0037701 A1 | 2/2008 | Banks | |
| 2008/0056440 A1 | 3/2008 | Fischer et al. | |
| 2008/0101533 A1 | 5/2008 | Ein-Gal | |
| 2008/0205584 A1 | 8/2008 | Sukovic et al. | |
| 2008/0245972 A1 | 10/2008 | Drapeau | |
| 2009/0080604 A1 | 3/2009 | Shores et al. | |
| 2009/0128351 A1 | 5/2009 | Ma | |
| 2010/0278300 A1 | 11/2010 | Yorkston et al. | |
| 2010/0329534 A1 | 12/2010 | Biermann et al. | |
| 2011/0210261 A1 | 9/2011 | Maurer, Jr. | |
| 2011/0228901 A1 | 9/2011 | Yorkston et al. | |
| 2011/0280364 A1 | 11/2011 | Maschke | |
| 2012/0043475 A1 | 2/2012 | Ahn | |
| 2012/0059239 A1 | 3/2012 | Yamaguchi | |
| 2013/0004042 A1 | 1/2013 | Yang et al. | |
| 2015/0173703 A1 | 6/2015 | Siewerdsen et al. | |

FOREIGN PATENT DOCUMENTS

| | | |
|---|---|---|
| DE | 101 47 157 | 4/2003 |
| DE | 10146915 | 4/2003 |
| DE | 10 2005 013 832 | 8/2006 |
| DE | 10 2008 019 646 | 10/2009 |
| EP | 0 119 660 | 9/1984 |
| EP | 1016375 | 12/1999 |
| EP | 0 676 911 | 9/2000 |
| EP | 0 919 187 | 1/2005 |
| EP | 2127696 | 3/2009 |
| JP | 02-228946 | 9/1990 |
| JP | 05-192342 | 8/1993 |
| JP | H05-192342 | 8/1993 |
| JP | 07-023942 | 1/1995 |
| JP | H10-328173 | 12/1998 |
| JP | 2001-269332 | 10/2001 |
| JP | 2003-088523 | 3/2003 |
| JP | 2005-517486 | 6/2005 |
| JP | 2006-314605 | 11/2006 |
| JP | 2010-154992 | 7/2010 |
| JP | 2010-200929 | 9/2010 |
| JP | 2013-066784 | 4/2013 |
| WO | 95/21570 | 8/1995 |
| WO | 95/22241 | 8/1995 |
| WO | 95/31936 | 11/1995 |
| WO | 03/070101 | 8/2003 |
| WO | 2006/042211 | 4/2006 |
| WO | 2006/119420 A1 | 11/2006 |
| WO | 2010/078481 | 7/2010 |
| WO | 2011/126555 | 10/2011 |
| WO | 2011/156526 | 12/2011 |

OTHER PUBLICATIONS

International Search Report mailed Nov. 23, 2011, International Application No. PCT/US2011/000596, 2 pages.
Supplementary Search Report—Annex to the EP Search Report on EP Patent Application No. EP 10 77 2373, Mailed date Apr. 10, 2013, 2 pages.
International Search Report for International Application No. PCT/US2013/063670 mailed on Dec. 10, 2013, 3 pages.
International Search Report for International Application No. PCT/US2013/063673 mailed on Feb. 14, 2014, 4 pages.
International Search Report for International Application No. PCT/US2013/063666 mailed on Feb. 7, 2014, 3 pages.
International Search Report for International Application No. PCT/US2013/063662 mailed on Feb. 17, 2014, 3 pages.
Definitions-Merriam-Webster.com, Merriam-Webster, n.d. Wed, Aug. 2, 2016.
Page from website—www.planmed.com, 1 page, Mar. 2011.

* cited by examiner

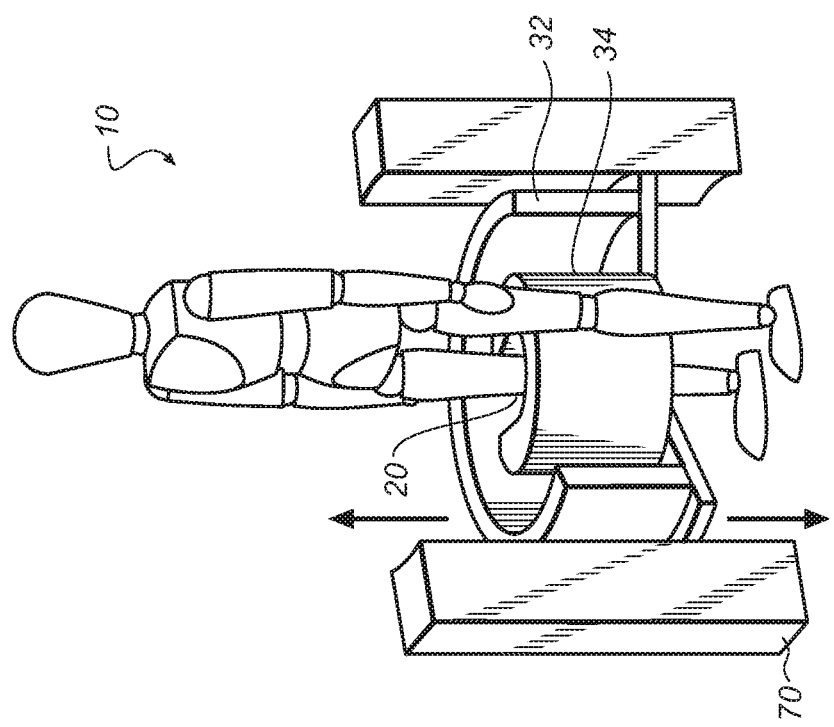

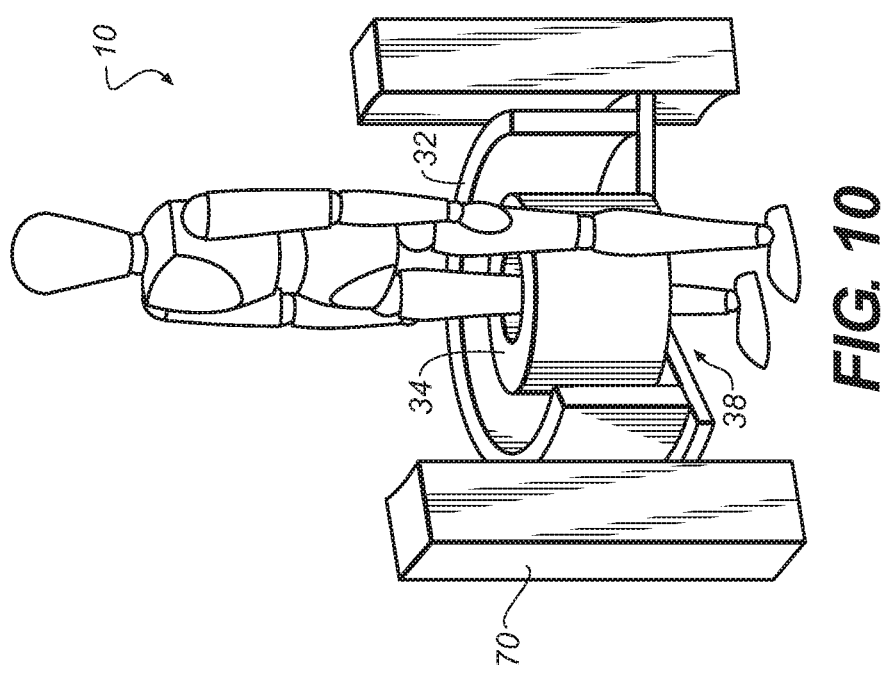

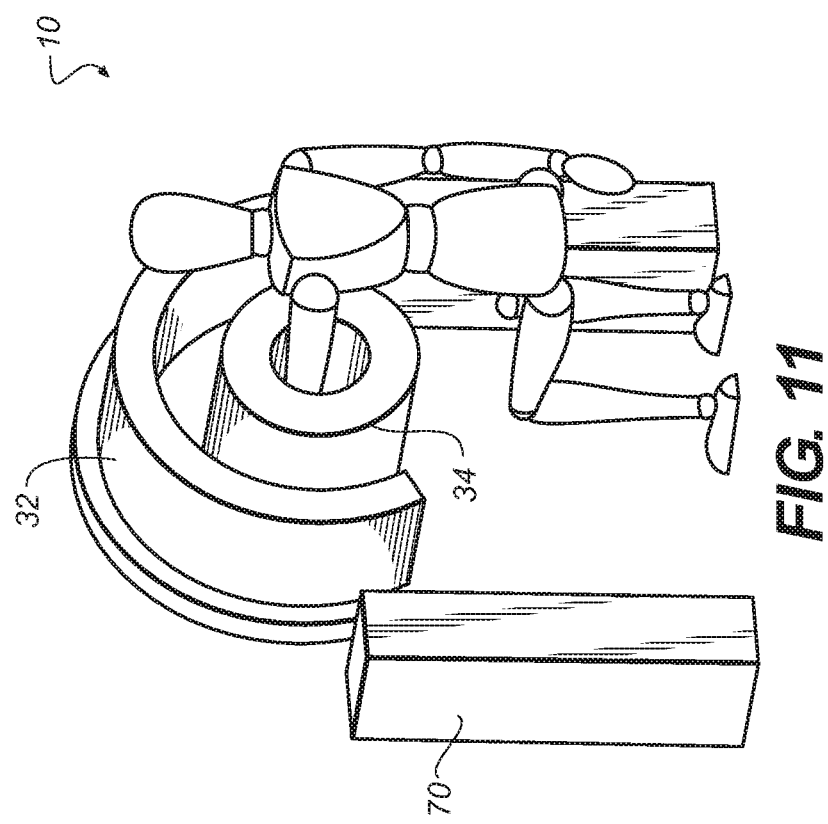

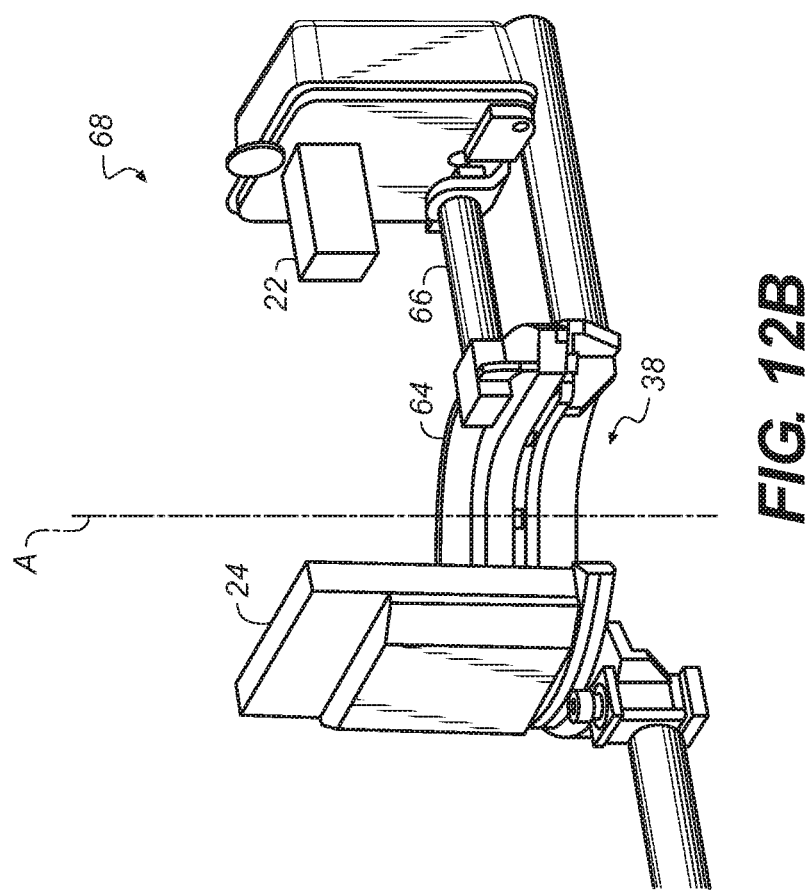

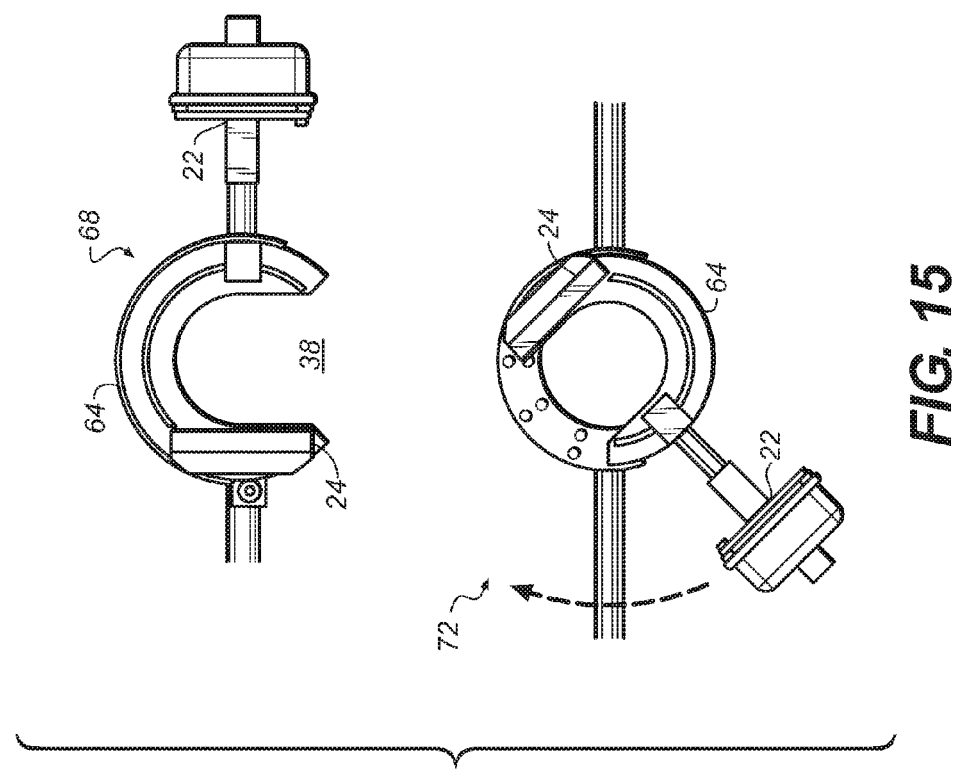

EXTREMITY IMAGING APPARATUS FOR CONE BEAM COMPUTED TOMOGRAPHY

CROSS REFERENCE TO RELATED APPLICATIONS

This patent application is a continuation of U.S. patent application Ser. No. 14/639,363, filed Mar. 5, 2015, in the name of Yorkston et al., entitled EXTREMITY IMAGING APPARATUS FOR CONE BEAM COMPUTED TOMOGRAPHY, which is a continuation of U.S. Pat. No. 8,998,486, filed May 1, 2014, in the name of Yorkston et al., entitled EXTREMITY IMAGING APPARATUS FOR CONE BEAM COMPUTED TOMOGRAPHY, which is a continuation of U.S. Pat. No. 8,746,972, filed Nov. 20, 2012, in the name of Yorkston et al., entitled EXTREMITY IMAGING APPARATUS FOR CONE BEAM COMPUTED TOMOGRAPHY, which is a continuation of U.S. Pat. No. 8,348,506, filed Apr. 30, 2010, in the name of Yorkston et al., entitled EXTREMITY IMAGING APPARATUS FOR CONE BEAM COMPUTED TOMOGRAPHY, which claims the benefit of U.S. Ser. No. 61/175,091 provisionally filed on May 4, 2009, in the names of Yorkston et al., entitled Cone Beam Computed Tomography (CBCT) For Extremity Imaging, which is hereby incorporated herein by reference in its entirety.

FIELD OF THE INVENTION

The invention relates generally to diagnostic imaging and in particular to cone beam imaging systems used for obtaining volume images of extremities.

BACKGROUND OF THE INVENTION

3-D volume imaging has proved to be a valuable diagnostic tool that offers significant advantages over earlier 2-D radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Cone beam (CB) computed tomography (CT) (CBCT) or cone beam CT technology offers considerable promise as one type of diagnostic tool for providing 3-D volume images. Cone beam CT systems capture volumetric data sets by using a high frame rate digital radiography (DR) detector and an x-ray source, typically affixed to a gantry that rotates about the object to be imaged, directing, from various points along its orbit around the subject, a divergent cone beam of x-rays toward the subject. The CBCT system captures projections throughout the rotation, for example, one 2-D projection image at every degree of rotation. The projections are then reconstructed into a 3D volume image using various techniques. Among the most common methods for reconstructing the 3-D volume image are filtered back projection approaches.

Although 3-D images of diagnostic quality can be generated using CBCT systems and technology, a number of technical challenges remain. In some cases, for example, there can be a limited range of angular rotation of the x-ray source and detector with respect to the subject. CBCT Imaging of legs, arms, and other extremities can be hampered by physical obstruction from a paired extremity. This is an obstacle that is encountered in obtaining CBCT image projections for the human leg or knee, for example. Not all imaging positions around the knee are accessible; the patient's own anatomy prevents the radiation source and image detector from being positioned over a portion of the scan circumference.

To illustrate the issues faced in CBCT imaging of the knee, the top view of FIG. 1 shows the circular scan paths for a radiation source 22 and detector 24 when imaging the right knee R of a patient as a subject 20. Various positions of radiation source 22 and detector are shown in dashed line form. Source 22, placed at some distance from the knee, can be positioned at different points over an arc of about 200 degrees; with any larger arc, left knee L blocks the way. Detector 24, smaller than source 22 and typically placed very near subject 20, can be positioned between the patient's right and left knees and is thus capable of positioning over the full circular orbit.

A full 360 degree orbit of the source and detector is not needed for conventional CBCT imaging; instead, sufficient information for image reconstruction can be obtained with an orbital scan range that just exceeds 180 degrees by the angle of the cone beam itself, for example. However, in some cases it can be difficult to obtain much more than about 180 degree revolution for imaging the knee or other joints and other applications. Moreover, there can be diagnostic situations in which obtaining projection images over a certain range of angles has advantages, but patient anatomy blocks the source, detector, or both from imaging over that range.

For imaging the leg, one way around this problem is to arrange the patient in a pose such that the subject leg is extended into a CBCT scanning apparatus and the paired leg is supported in some other way or bent with respect to the subject leg, such as at a right angle. This is the approach used, for example, in the CT scanner device taught in U.S. Pat. No. 7,394,888 entitled "CT Scanner for Lower Extremities" to Sukovic et al. In the methods of the Sukovic et al. '888 disclosure, the other leg must either be lifted out of place or spread at a distance, or is relaxed while the subject leg is lifted out of place and extended into the scanner equipment. This arrangement can be particularly disadvantageous for a number of reasons. It can be helpful, for example, to examine the condition of a knee or ankle joint under the normal weight load exerted on that joint by the patient. But, in requiring the patient to assume a position that is not usually encountered in typical movement, the Sukovic et al. '888 apparatus may obtain an image when there is excessive strain, or insufficient strain, or poorly directed strain, on the joint.

Another issue with conventional approaches relates to imaging of a load-bearing extremity such as the human leg. Because of the inability to image the leg under a normal load, as the patient is in a standing position, various artificial ways of mimicking load conditions have been attempted. Such approaches have used various types of braces, compression devices, and supports. As one example intended to remedy the shortcomings of conventional imaging techniques, the Sukovic et al. '888 disclosure teaches simulating the normal loading of the leg by elevating the leg to a non-standing position, then applying an external force against the leg. However, it can be readily appreciated that while this type of simulation allows some approximation of load-bearing limb response, it can be inaccurate. The knee or ankle joint, under some artificially applied load and at an angle not taken when standing, may not behave exactly as it does when bearing the patient's weight in a standing position.

Another difficulty with the Sukovic et al. '888 apparatus and with other devices designed to address knee and lower leg imaging relates to poor image quality. For image quality, the CBCT sequence requires that the detector be up close to the subject and the source of the cone beam radiation be at a sufficient distance from the subject. This provides the best image and reduces image truncation and consequent lost data. Positioning the subject midway between the detector and the source, as Sukovic et al. '888 apparatus and with other devices require, not only noticeably compromises image quality, but also places the patient too near the radiation source, so that radiation levels are considerably higher. One example of this strategy is shown in German patent publication DE 10146915. With the C-shaped gantry arrangement shown, centering the subject at the center of rotation of source and detector would apply considerably higher radiation amounts with each projection and severely compromise image quality. Any other positioning of the subject, such as closer to the detector, might reduce radiation levels over some part of the image capture sequence, but would result in unduly complex image reconstruction problems, since this would actually vary the distances between radiation source and subject and between subject and detector with each projection image obtained. Attempted imaging of the knee with such a system would require the patient to be supported in some way, balancing on the leg being imaged. It can be appreciated that this requirement is unreasonable or impossible for many situations in which an injured knee is being imaged. Thus, the C-shaped gantry shown would not be suitable for imaging only one knee of the patient.

Imaging of the foot and ankle presents additional obstacles for CBCT projection image capture. Approaches such as that given in the Sukovic et al. '888 disclosure, centering the foot between source and detector, suffer from the same problems of poorly positioned exposure and noticeably compromised image quality.

In summary, for extremity imaging, particularly for imaging the lower paired extremities, a number of improvements are needed, including the following: (i) improved placement of the radiation source and detector to provide acceptable radiation levels and image quality throughout the scanning sequence; (ii) system flexibility for imaging at different heights with respect to the rotational axis of the source and detector, including the flexibility to allow imaging with the patient standing or seated comfortably, such as with a foot in an elevated position, for example; (iii) improved patient accessibility, so that the patient does not need to contort, twist, or unduly stress limbs or joints that may have been injured in order to provide images of those body parts; (iv) improved ergonomics for obtaining the CBCT image, allowing the patient to stand with normal posture, for example. This would also allow load-bearing extremities, such as legs, knees, and ankles, to be imaged under the normal load exerted by the patient's weight, rather than under simulated loading conditions as taught in the Sukovic et al. '888 disclosure and elsewhere.

Thus, it can be seen that although a number of solutions have been proposed to address the problem of CBCT extremity imaging, conventional solutions fall short of what is needed for both usability and performance.

SUMMARY OF THE INVENTION

It is an object of the present invention to advance the art of diagnostic imaging of extremity body parts, particularly jointed or load-bearing, paired extremities such as knees, legs, ankles, fingers, hands, wrists, elbows, arms, and shoulders.

It is a feature of the present invention that it provides an apparatus with different radii for orbital paths of sensor and radiation source components.

It is an advantage of the present invention that it allows imaging of load-bearing extremities for a patient who is standing.

From one aspect, the present invention provides apparatus for cone beam computed tomography of an extremity of a patient, the apparatus comprising: a digital radiation detector; a first device to move the detector along at least a portion of a circular detector path, the portion of the detector path extending so that the detector moves both at least partially around a first extremity of the patient and between the first extremity and a second, adjacent extremity of the patient, the detector path having a radius $R_1$ that is sufficiently long to allow the first extremity of the patient to be positioned approximately at a center of the detector path; a radiation source; a second device to move the source along at least a portion of a concentric circular source path having a radius $R_2$ greater than radius $R_1$, radius $R_2$ being sufficiently long to allow adequate radiation exposure of the first extremity for an image capture by the detector; and a first circumferential gap in the source path to allow the second extremity to be positioned in the first circumferential gap during the image capture.

According to another aspect, the present invention provides an apparatus for cone beam computed tomography of a portion of a subject leg of a patient who is standing on the subject leg and its paired leg, the apparatus comprising: a digital radiation detector; a detector transport that defines a detector path for movement of the digital radiation detector along a first circular arc, wherein the first circular arc has a radius R1 with respect to a central point within the subject leg and wherein the first circular arc extends through the space between the subject leg and its paired leg; a radiation source; a radiation source transport that defines a radiation source path for movement of the radiation source along a second circular arc of a second radius R2, larger than radius R1, with respect to the central point in the subject leg, wherein the second circular arc lies outside the space between the subject leg and its paired leg; and a circumferential gap in the radiation source path for placement of the subject leg.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 7 is a perspective view showing optional height adjustment.

FIG. 10 is a perspective view that shows imaging with the detector transport fully encircling the lower extremity.

FIG. 11 is a perspective view that shows imaging with the detector transport fully encircling the upper extremity.

FIG. 12B is a perspective view of an imaging apparatus using a turntable for source and detector transport.

FIG. 15 shows top views of the turntable transport arrangement for initial positioning of the extremity of the patient and beginning of scan.

DETAILED DESCRIPTION OF THE INVENTION

Figure 1:
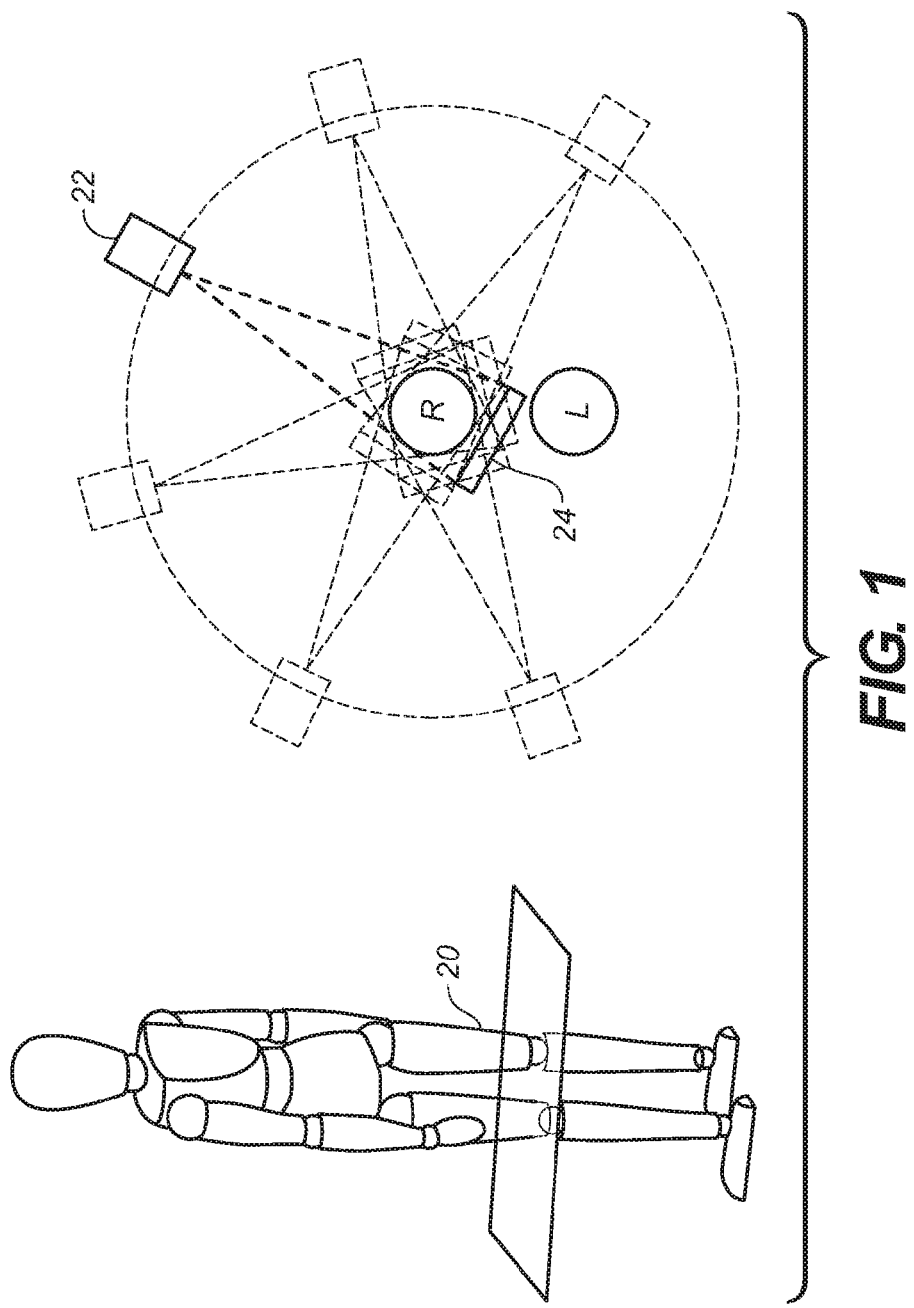
FIG. 1 is a schematic view showing the geometry and limitations of CBCT scanning for portions of the lower leg.

The following is a detailed description of the preferred embodiments of the invention, reference being made to the drawings in which the same reference numerals identify the same elements of structure in each of the several figures.

In the context of the present disclosure, the term "extremity" has its meaning as conventionally understood in diagnostic imaging parlance, referring to knees, legs, ankles, fingers, hands, wrists, elbows, arms, and shoulders and any other anatomical extremity. The term "subject" is used to describe the extremity of the patient that is imaged, such as the "subject leg", for example. The term "paired extremity" is used in general to refer to any anatomical extremity wherein normally two or more are present on the same patient. In the context of the present invention, the paired extremity is not imaged; only the subject extremity is imaged.

To describe the present invention in detail, the examples given herein for embodiments of the present invention focus on imaging of the load-bearing lower extremities of the human anatomy, such as the leg, the knee, the ankle, and the foot, for example. However, these examples are considered to be illustrative and non-limiting.

In the context of the present disclosure, the term "arc" or, alternately, "circular arc", has its conventional meaning as being a portion of a circle of less than 360 degrees or, considered alternately, of less than 2π radians for a given radius.

Embodiments of the present invention address the difficulties of lower extremity imaging by providing an imaging apparatus that defines orbital source and detector paths, concentric about a center point, wherein components that provide the source and detector paths are configured to allow patient access prior to and following imaging and configured to allow the patient to stand with normal posture during the CBCT image capture series. In embodiments of the present invention, this capability is effected by using a detector transport device that has a circumferential access opening allowing positioning of the extremity, wherein the detector transport device is revolved about the positioned extremity once it is in place, enclosing the extremity as it is revolved through at least a portion of the scan.

It is instructive to consider dimensional attributes of the human frame that can be considerations for design of CBCT equipment for scanning extremities. For example, an adult human patient of average height in a comfortable standing position has left and right knees generally anywhere from about 10 to about 35 cm apart. For an adult of average height, exceeding about 35-40 cm (14-15.7 inches) between the knees becomes increasing less comfortable and out of the range of normal standing posture. It is instructive to note that this constraint makes it impractical to use gantry solutions such as that shown in DE 10146915, described earlier, for knee imaging. Either the source or the detector must be able to pass between the legs of a standing patient for knee CBCT imaging, a capability not available with gantry or other conventional solutions.

Figure 2:
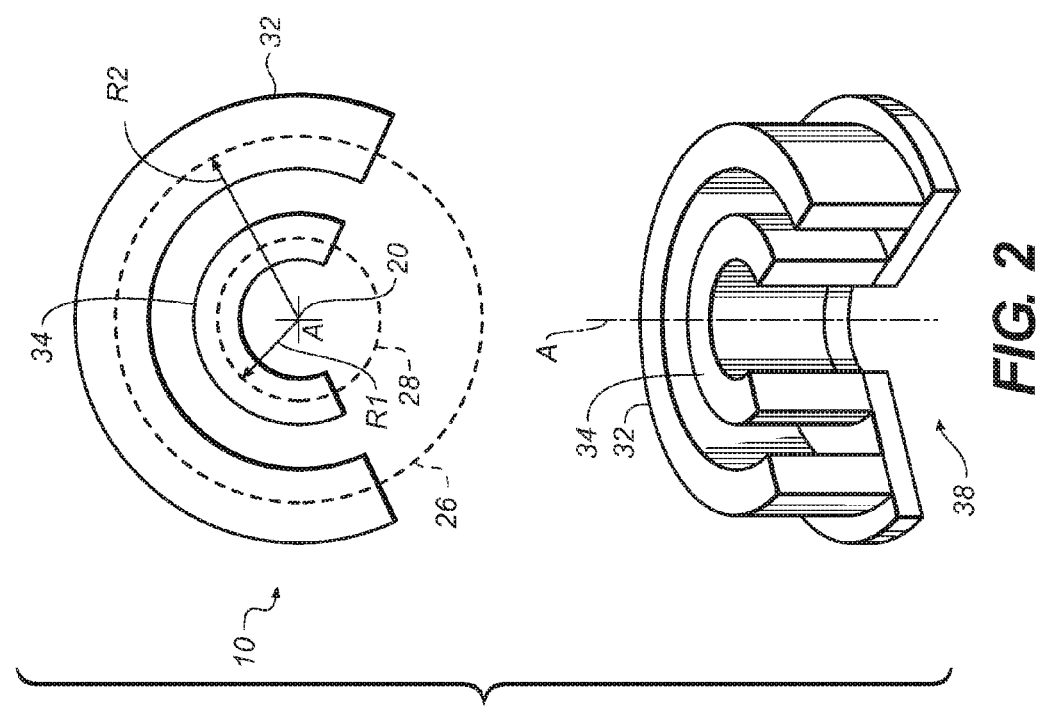
FIG. 2 shows a top and perspective view of the scanning pattern for an imaging apparatus according to an embodiment of the present invention.

The perspective and top views of FIG. 2 show how the scanning pattern is provided using various embodiments of a CBCT imaging apparatus 10 according to the present invention. A detector path 28 of a suitable radius R1 from a central axis A is provided by a first device, a detector transport 34. A source path 26 of a second, larger radius R2 is provided by a second device, a source transport 32. The extremity, subject 20, is substantially centered along central axis A so that central axis A can be considered as a line through points in subject 20. The limiting geometry for image capture is due to the arc of source transport 32, blocked by patient anatomy, such as by a paired limb, to typically about 200 degrees, as noted previously. This defines a partial circular sector, bounded by this arc and radii at start and end-of-scan.

Figure 3:
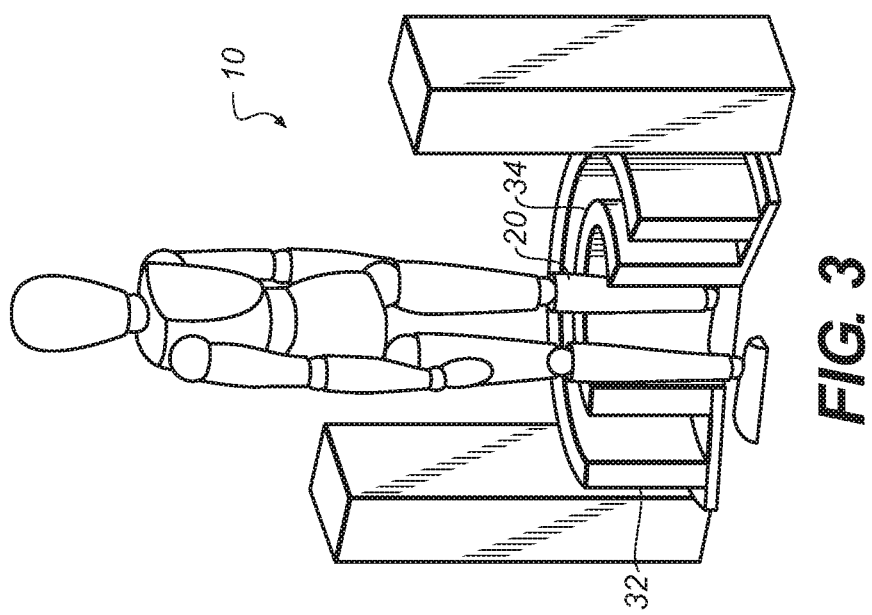
FIG. 3 is a perspective view showing patient access to an imaging apparatus according to an embodiment of the present invention.
Figure 4:
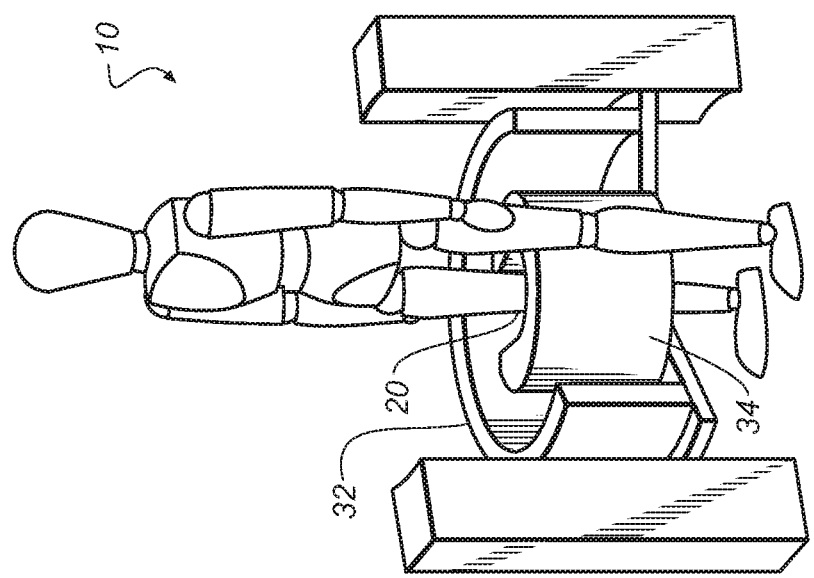
FIG. 4 is a perspective view showing the patient in a scanning position.

Detector transport 34, while capable of a fully circular orbit because it can be moved between the standing patient's legs, follows the necessary complementary arc to that of source transport 32. Patient access before scanning is eased by providing a circumferential gap 38 in detector transport 34. With detector transport 34 in the open position shown in FIG. 3, the patient can freely move in and out of position for imaging. When the patient is properly in position, detector transport 34 is revolved about axis A, substantially 180 degrees. This orbital movement confines the extremity more narrowly and places detector 24, not visible in FIGS. 2-4 due to the detector transport 34 housing, in position near subject 20 for obtaining the first projection image in sequence.

Circumferential gap 38 not only allows access for positioning of the subject leg or other extremity, but also allows sufficient space for the patient to stand in normal posture during imaging, placing the subject leg for imaging in the central position of axis A (FIG. 2) and the non-imaged paired leg within the space defined by circumferential gap 38.

Circumferential gap 38 extends approximately 180 degrees plus the fan angle, which is determined by source-detector geometry and distance.

Figure 5:
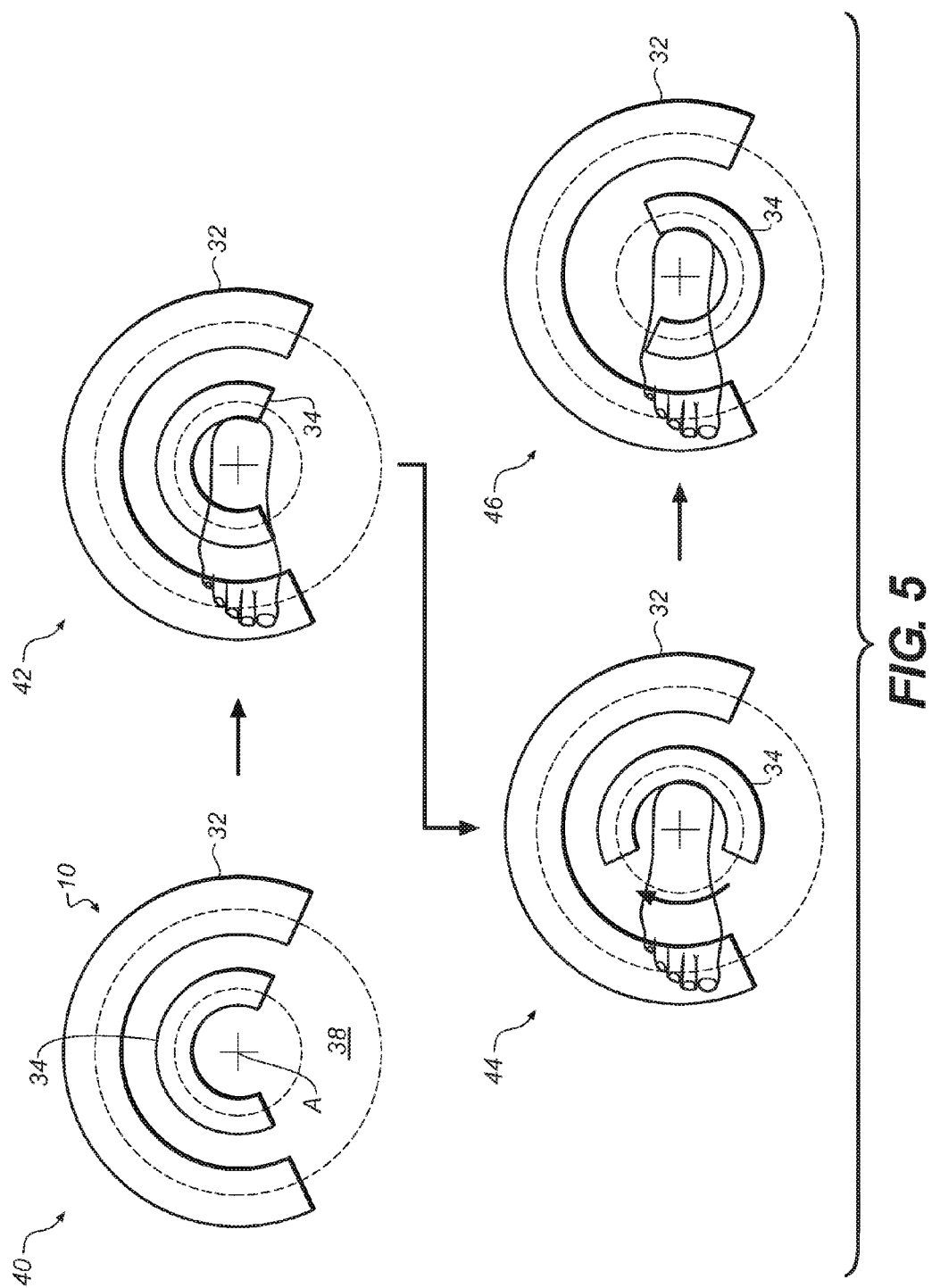
FIG. 5 is a series of top schematic views showing the sequence for patient access and system preparation for CBCT imaging.

The top views of FIG. 5 show the sequence for patient access for imaging apparatus 10. In an open access position 40, circumferential gap 38 permits access of the extremity so that it can be centered in position along central axis A. The outline of the foot corresponding to an open access position 42 indicates positioning of the patient and is shown for reference. In this example, the left leg is the subject imaged; the paired right leg would lie within or just outside circumferential gap 38. Once the patient's leg or other extremity is in place, detector transport 34, or a hooded cover or other member that defines this transport path, can be revolved into position, closing the detector portion of circumferential gap 38, as shown in a revolving transport position 44. A transport in place position 46 shows detector transport 34 in suitable position for executing the CBCT imaging sequence.

Figure 6:
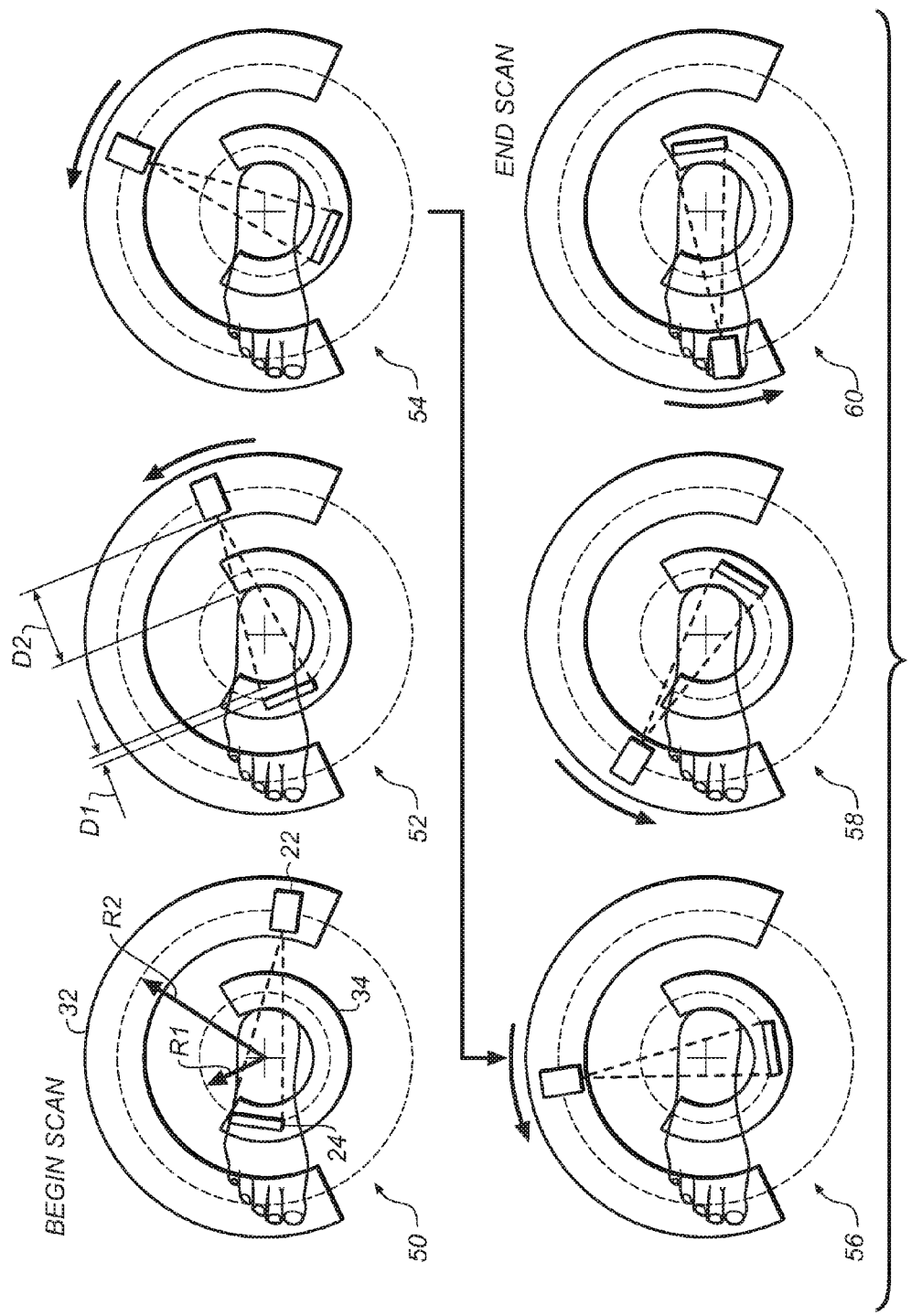
FIG. 6 is a series of top schematic views showing the sequence for obtaining CBCT projections at a number of angular positions.

The top views of FIG. 6 continue the operational sequence begun in FIG. 5 and show the sequence for obtaining CBCT projections at a number of angular positions when using imaging apparatus 10. The relative positions of radiation source 22 and detector 24, which may be concealed under a hood, as noted earlier, are shown in FIG. 6. The source and detector are diametrically opposite at each position during the CBCT scan and projection imaging. The sequence begins at a begin scan position 50, with radiation source 22 and detector 24 at initial positions to obtain an image at a first angle. Then, both radiation source 22 and detector 24 revolve about axis A as represented in interim scan positions 52, 54, 56, and 58. Imaging terminates at an end scan position 60. As this sequence shows, source 22 and detector 24 are in diametrically opposing positions relative to subject 20 at each imaging angle. Throughout the scanning cycle, detector 24 is within a short distance D1 of subject 20. Source 22 is positioned beyond a longer distance D2 of subject 20. The positioning of source and detector components can be carried out by separate actuators, one for each transport path, or by a single rotatable member, as described in more detail subsequently. It should be noted that scanning motion in the opposite direction, that is, clockwise with respect to the example shown in FIG. 6, is also possible, with the corresponding changes in initial and terminal scan positions.

Other features of imaging apparatus 10 are provided by the capability to move both source and detector transports 32 and 34 along the axis direction as a unit, as shown in the perspective view of FIG. 7. A vertical support 70 provides vertical transport of the imaging apparatus, so that the source and detector can be translated upwards or downwards in the direction of the central axis in order to suit patients of different heights and to image different portions of the leg. The height adjustment can be made before or after the patient's subject leg to be imaged is enclosed by detector transport 34 using the setup sequence of FIG. 5.

Figure 8B:
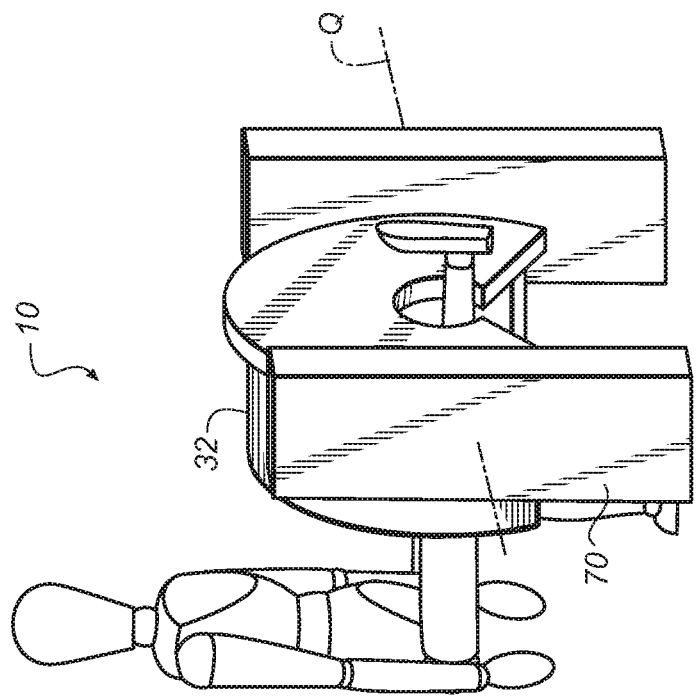
FIGS. 8A and 8B are perspective views that show extremity imaging for an extended leg in an alternate configuration.
Figure 8A:
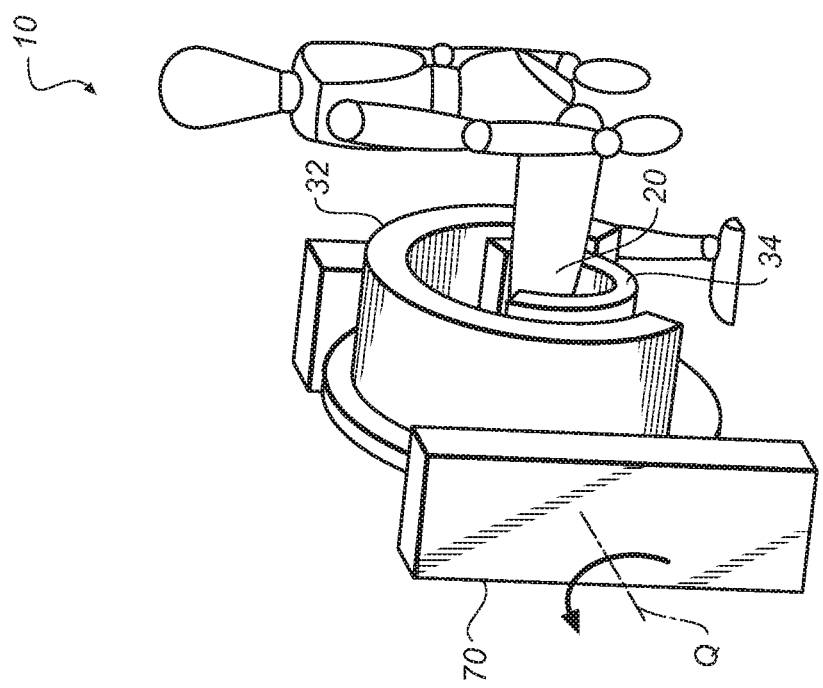
Figure 9:
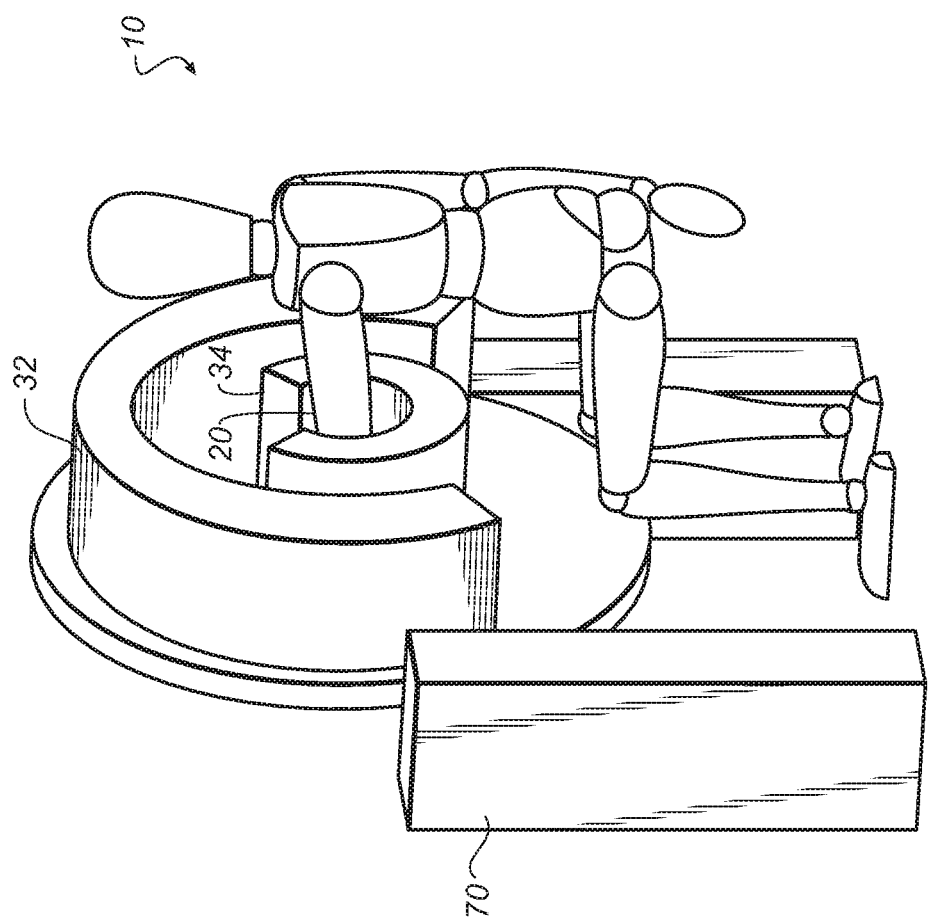
FIG. 9 is a perspective view that shows a configuration of the imaging apparatus for upper extremity imaging.

In one embodiment, vertical support 70 also allows rotation of the CBCT imaging apparatus 10 to allow imaging of an extremity that is disposed horizontally or is extended at some oblique angle other than vertical. FIGS. 8A and 8B show perspective views of knee imaging in a horizontal position, with the patient seated and the leg outwardly extended. Full 360 degree rotation about an axis Q is possible. It should be noted that, with this application, similar patient accessibility applies, with detector transport 34 revolved into position once the extremity is centered in place. Further height adjustment is also possible, such as for arm, elbow, or shoulder imaging, as shown in FIG. 9.

Using revolving detector transport 34 simplifies patient access and provides sufficient imaging path for CBCT imaging, since the angular limitation of the orbital imaging path is due to source obstruction, rather than to the detector path. Thus, for example, detector transport 34 could fully encircle the limb, as shown in the examples of FIGS. 10 and 11. In these embodiments, there is a circumferential gap 38 only in the source orbit.

Referring back to the schematic diagrams of FIG. 6, radiation source 22 and detector 24 each orbit the subject along an arc with radii R2 and R1, respectively. Within source transport 32, a source actuator could be used, cooperating with a separate, complementary detector actuator that is part of detector transport 34. Thus, two independent actuator devices, one in each transport assembly, can be separately controlled and coordinated by an external logic controller to move source 22 and detector 24 along their respective arcs, in unison, about subject 20.

Figure 12A:
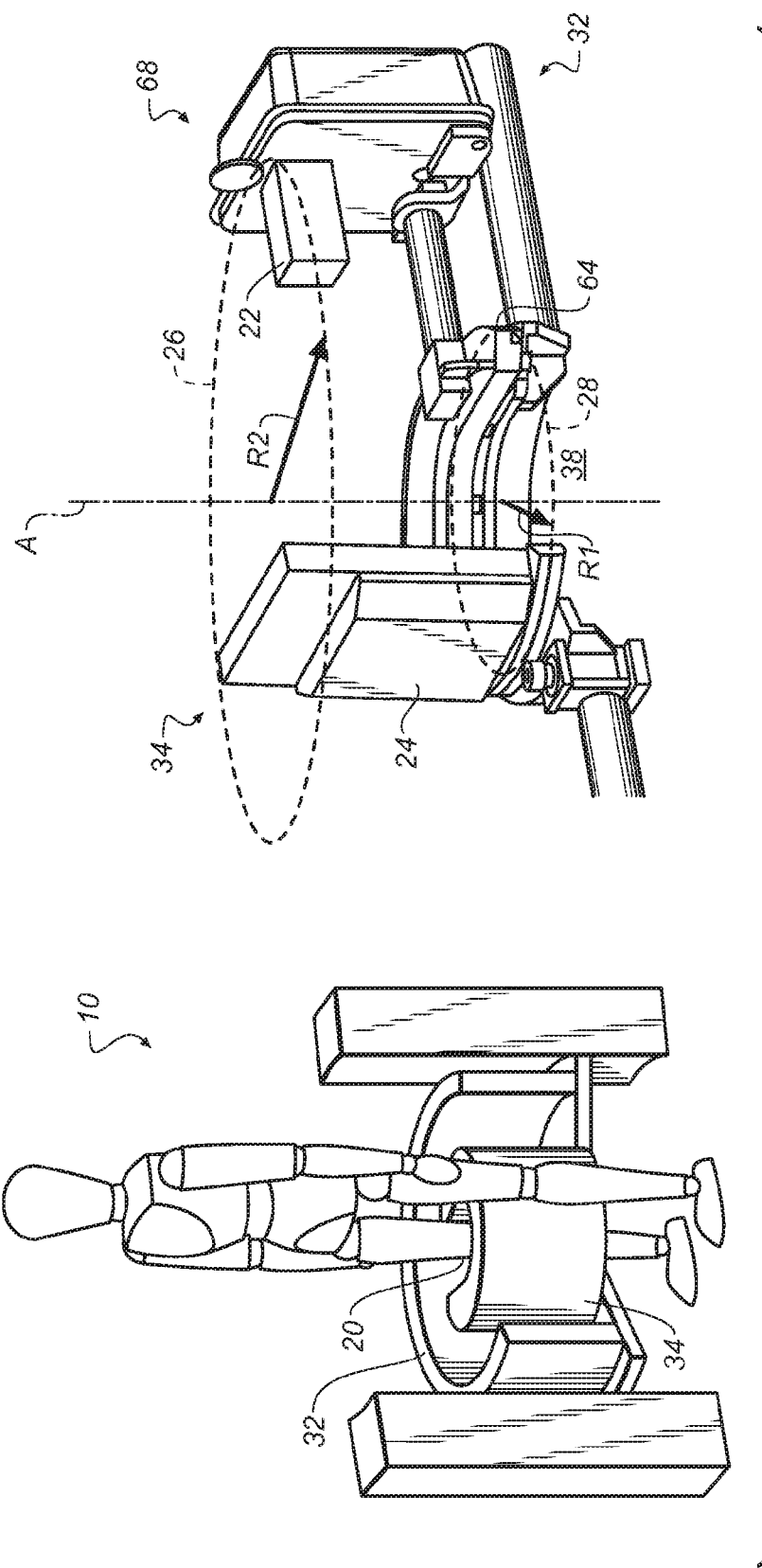
FIG. 12A shows perspective views of imaging apparatus with and without covers.

In an alternate embodiment, source and detector transport components are mechanically linked to a single revolving or rotating assembly. One such arrangement, shown at the right in FIG. 12A and enlarged in FIG. 12B, provides source and detector transports 32 and 34 using a single mechanical assembly, a rotating member 68, on a turntable 64 that revolves about central axis of rotation A and provides the needed radii for source 22 and detector 24. As is best shown in the top view of FIG. 13, detector 24 rides along the surface of the C-shaped turntable 64, orbiting the subject at radius R1. Source 22 is connected to turntable 64 along an arm 66 that provides the longer radius R2. Circumferential gap 38 extends across both source and detector paths.

It should be emphasized that the embodiments shown using rotating member 68 on turntable 64 can be encased in one or more housings, thereby providing similar appearance to imaging apparatus 10 shown in FIGS. 7-11, for example. This type of arrangement has advantages for isolating the patient from moving components and for alleviating at least some of the patient anxiety that might be caused by automatically moving components during imaging.

Figure 14A:
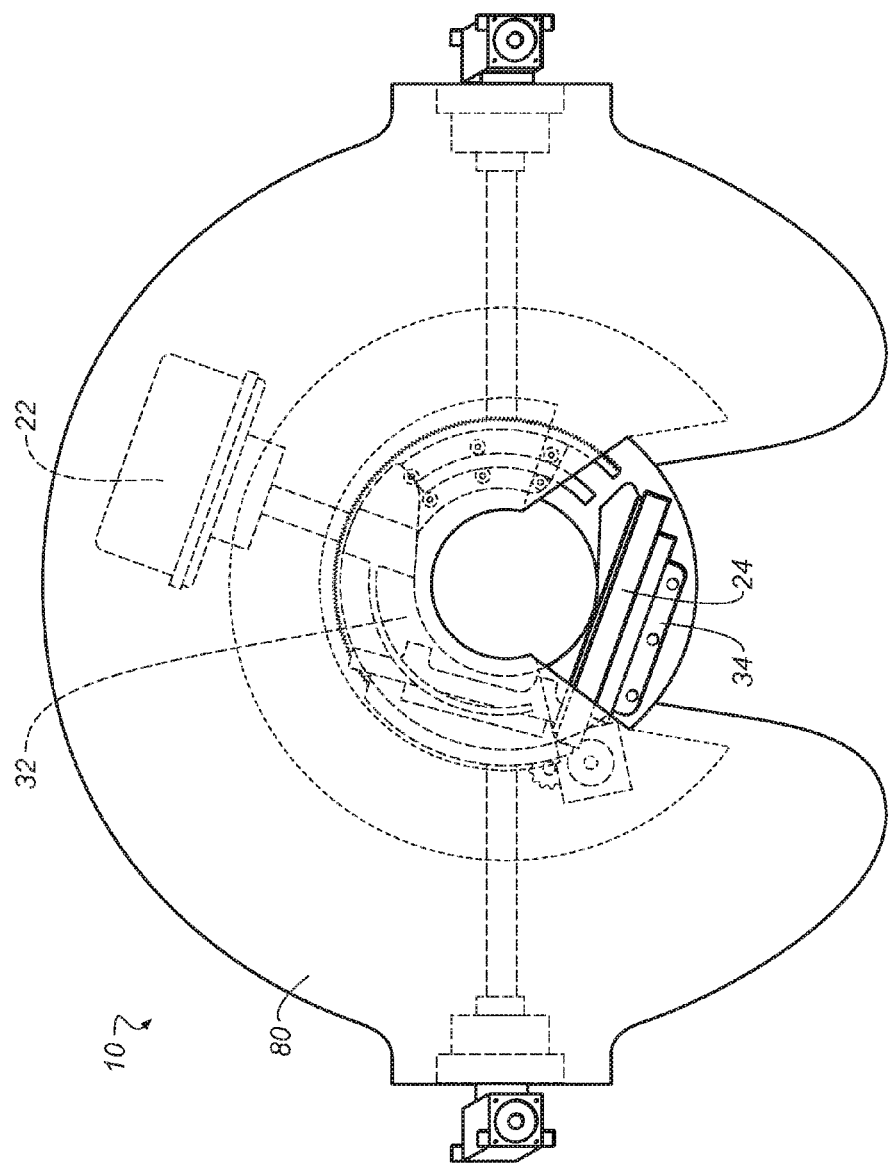
FIG. 14A shows a top view of the imaging apparatus with the hood partially transparent.
Figure 14B:
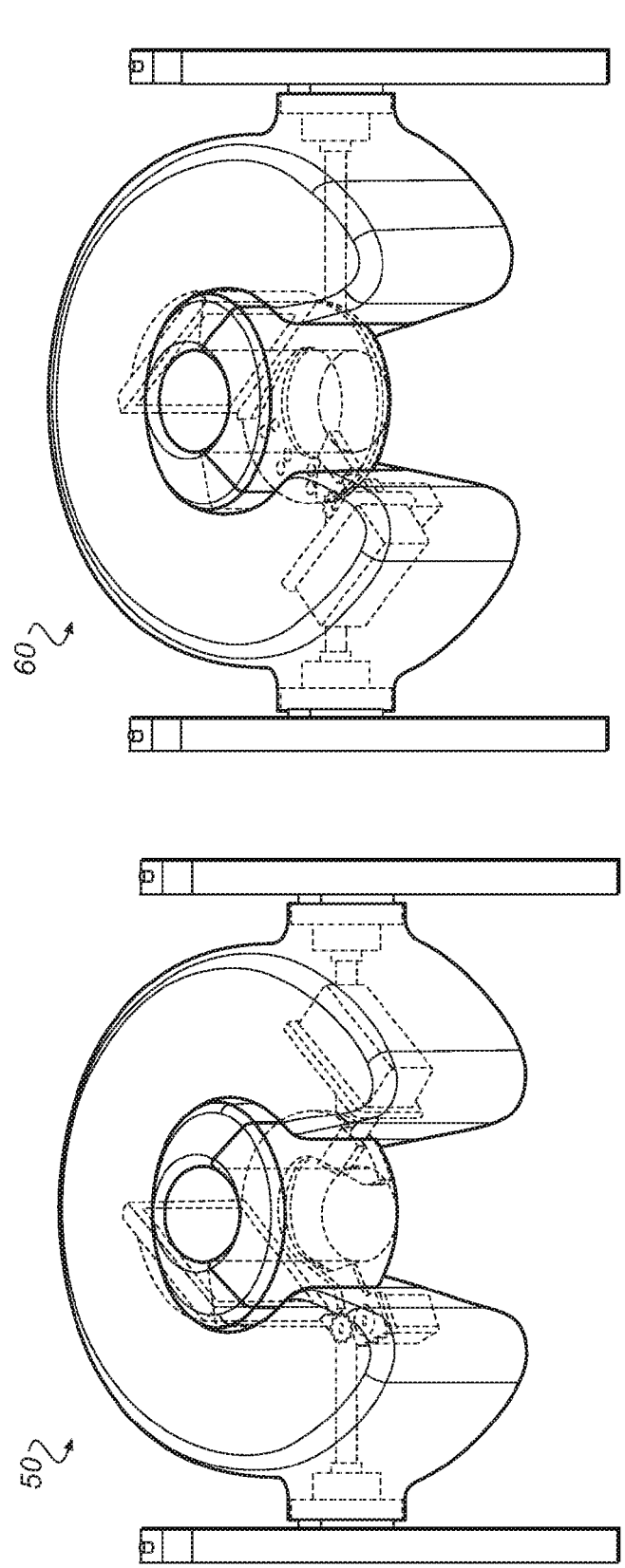
FIG. 14B shows internal components in start and stop scan positions.

FIG. 14A shows sources and detector transports 32 and 34 and source and detector 22 and 24 components as they are fitted within covers 80 that protect moving mechanical parts and help to prevent patient contact with moving components. FIG. 14B shows the covered system with internal components in begin and end scan positions 50 and 60 respectively, when using the scan sequence described earlier with reference to FIG. 6.

Figure 13:
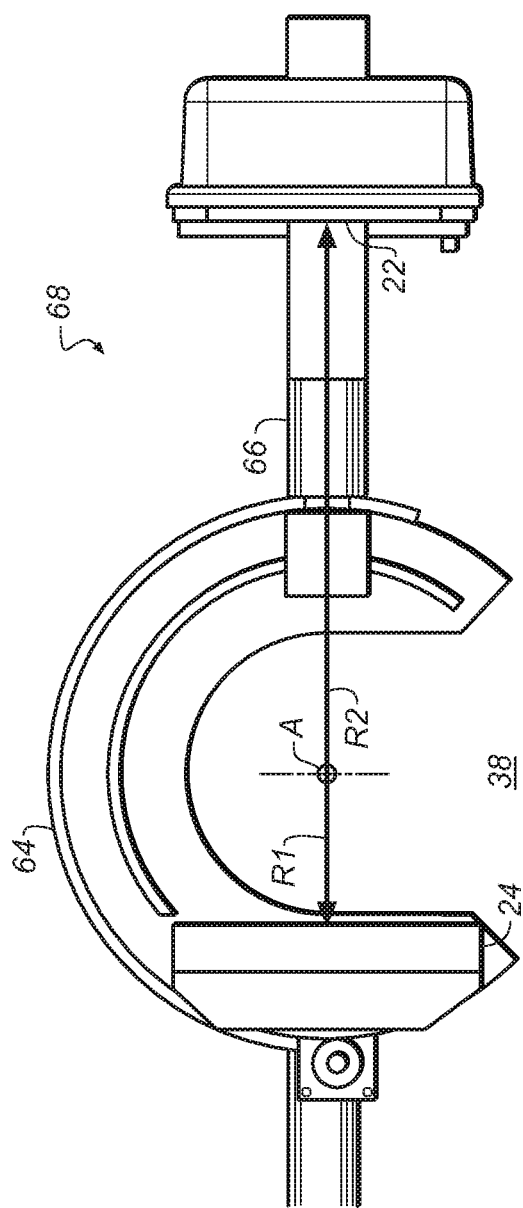
FIG. 13 is a top view of the transport arrangement shown in FIG. 12B.
Figure 16:
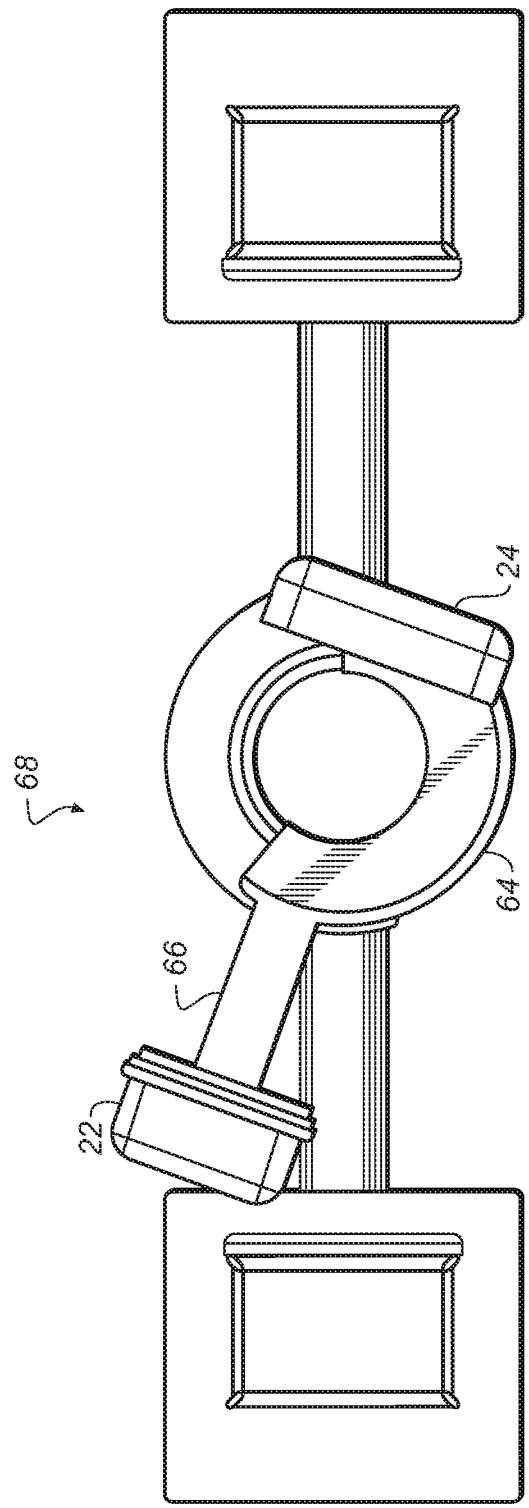
FIG. 16 shows a top view during the scan sequence.

The top views of FIGS. 13, 15, and 16 show how patient access is provided using this mechanical arrangement. Once the patient is positioned, rotating member 68 is swung around the positioned extremity, to a start position 72, as shown at the bottom in FIG. 15. Imaging begins at this position and continues as rotating member 68 revolves source and detector components about axis A. For the example of FIGS. 15 and 16, rotating member 68 moves in a clockwise direction. Counter-clockwise rotation would also be possible.

Figure 17:
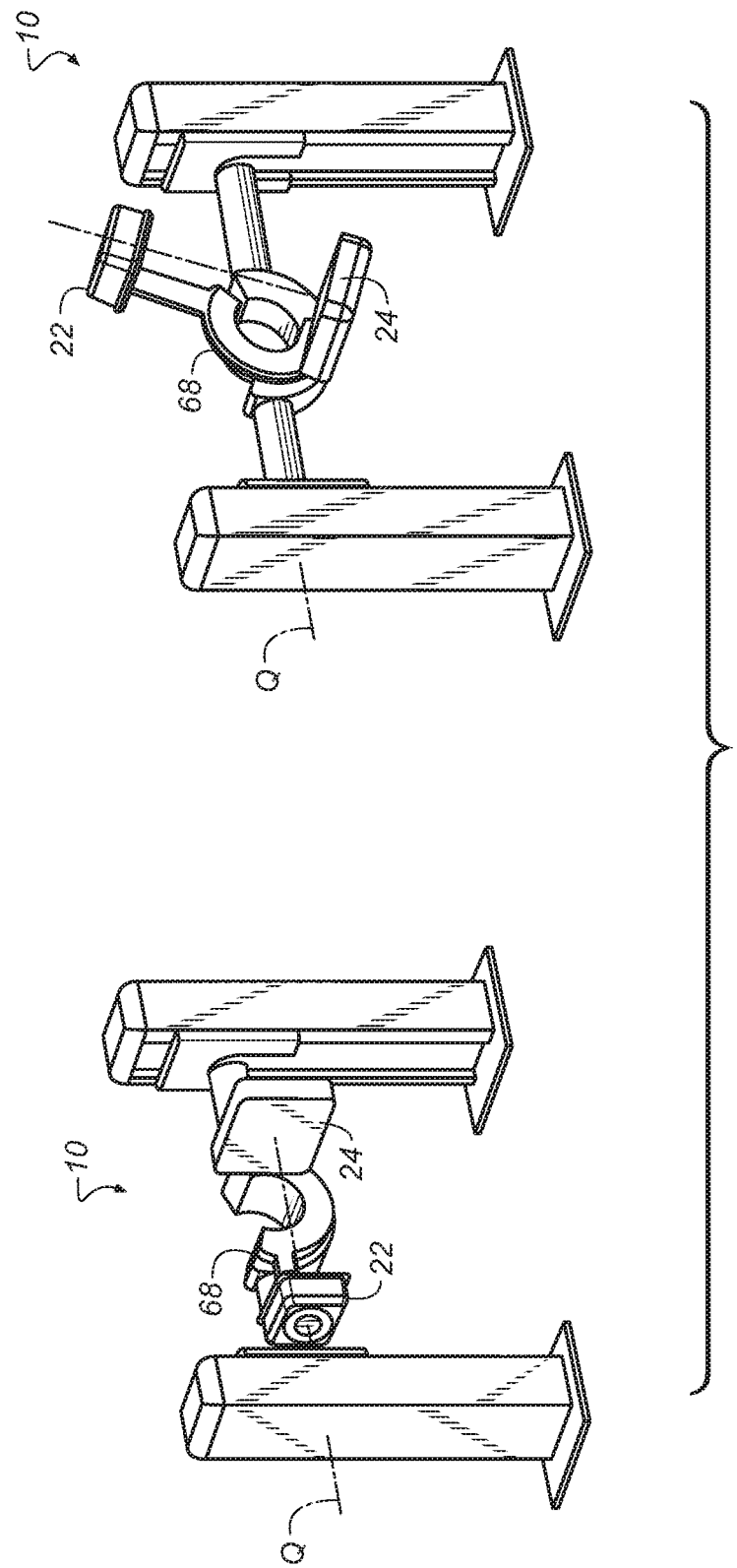
FIG. 17 shows perspective views of an embodiment for extremity imaging at a horizontal position.

Rotating member 68 can also be used with an imaging configuration for upper extremities, as shown in FIG. 17. Because none of the patient anatomy blocks the transport path, a full circular orbit is permitted for scanning with this configuration. Again, full 360 degree rotation of the components in the plane of rotating member 68 is possible, about axis Q.

Figure 18:
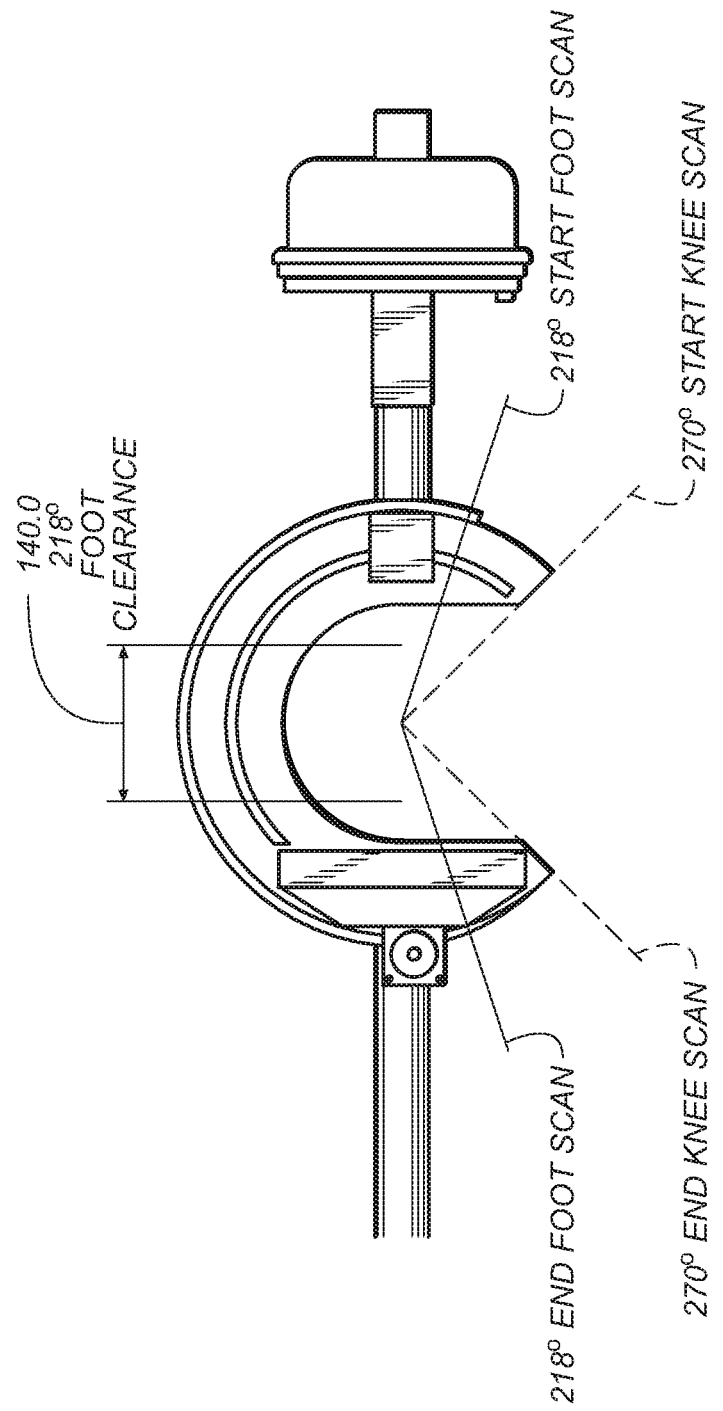
FIG. 18 is a top view that compares angular considerations for foot and knee imaging.

Imaging of the ankle and foot is also possible with CBCT imaging apparatus 10. However, because the foot protrudes outward into the desired detector transport path, the allowable angular range for foot imaging is more constrained than the range for leg and knee imaging. The top view of FIG. 18 shows, for example, that the angular range for CBCT scanning of the foot, for a standing patient, is about 50 degrees less than that for knee imaging, for example.

A range of optional devices can also be provided to facilitate the imaging process. For example, a horizontal or vertical foot support can be provided for support of the patient's foot. Optionally, the foot support can be adjustable to some oblique angle between horizontal and vertical, such as at a 33 degree or 45 degree angle for example.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

10. CBCT imaging apparatus
20. Subject
22. Source
24. Detector
26. Source path
28. Detector path
32. Source transport
34. Detector transport
38. Circumferential gap
40. Open access position
42. Open access position
44. Revolving transport position
46. Transport in place position
50. Begin scan position
52, 54, 56, 58. Interim scan position
60. End scan position
64. Turntable
66. Arm
68. Rotating member
70. Vertical support
72. Start position
74. Foot insert member
80. Cover
A. Central axis
D1, D2. Distance
L. Left knee
Q. Axis
R. Right knee
R1, R2. Radius

What is claimed is:

1. A method for cone beam computed tomography, the method comprising:
moving a digital radiation detector along at least a portion of a detector path, the at least a portion of the detector path extending so that the digital radiation detector is configured to move at least partially around a first extremity of a patient, the detector path having a distance D1 that is sufficiently long to allow the first extremity to be positioned within the detector path;
moving a radiation source along at least a portion of a source path outside the detector path, the source path having a distance D2 greater than the distance D1, the distance D2 being sufficiently long to allow adequate radiation exposure of the first extremity for an image capture by the digital radiation detector;
moving the radiation source at a source position along the source path in correspondence to a detector position for the detector along the detector path during the image capture; and
providing a first gap in the detector path.

2. The method according to claim 1, where the detector path, the detector, the source path and the radiation source are within a housing.

3. The method according to claim 1, comprising providing a second gap in the source path sized to allow a second, adjacent extremity to be positioned in the second gap during the image capture, the first gap having a circumferential length sufficient to allow the first extremity to pass through the first gap.

4. The method according to claim 1, further comprising a foot support that is adjustable for foot placement at an angular position that is horizontal, vertical, or at some angle that lies between horizontal and vertical, where the foot support is positioned operatively adjacent to the detector path.

5. The method according to claim 1, further comprising moving the source and detector along the first extremity or rotating the detector path and source path to a vertical or other angular orientation.

6. The method according to claim 1, further comprising revolving the source path and independently revolving the detector path, where the detector path can revolve to align the first gap with a second gap in the source path.

7. The method according to claim 6, where the first and second gaps each extend approximately 180 degrees plus the fan angle determined by radiation source and detector geometry and distance.

8. The method according to claim 1, where detector path and the source path are rigidly connected or movably connected.

9. An apparatus for cone beam computed tomography (CBCT), the apparatus comprising:
a digital radiation detector;
a first device to move the detector along at least a portion of a detector path, the at least a portion of the detector path extending so that the detector is configured to move at least partially around an imaging position of the CBCT apparatus, the detector path having a distance D1 that is sufficiently long to allow the imaging position of the CBCT apparatus to be positioned within the detector path;
a radiation source;
a second device to move the source along at least a portion of a source path outside the detector path, the source path having a distance D2 greater than the distance D1, the distance D2 being sufficiently long to allow adequate radiation exposure of the imaging position of the CBCT apparatus for an image capture by the detector; and
a first gap in the detector path.

10. The apparatus according to claim 9, where the detector path and the detector are within a first housing, and where the source path and the radiation source are within a second housing.

11. The apparatus according to claim 9, comprising a second gap in the source path sized to allow a second, adjacent extremity to be positioned in the second gap during the image capture, the first gap having a circumferential length sufficient to allow a first extremity of the patient to pass through the first gap into the imaging position of the CBCT apparatus.

12. The apparatus according to claim 9, wherein the first and second devices maintain the radiation source at a source position along the source path in correspondence to a detector position for the detector along the detector path during the image capture.

13. The apparatus according to claim 9, further comprising a foot support that is adjustable for foot placement at an angular position that is horizontal, vertical, or at some angle between horizontal and vertical, where the foot support is operatively adjacent the detector path.

14. The apparatus according to claim 9, further comprising a third device configured to move the source and detector along the first extremity and configured to rotate the detector path and source path to a vertical or other angular orientation.

15. The apparatus according to claim 9 where the first device is revolvable, where the second device is revolvable, and when the second device is revolved to one position a second gap in the source path is configured to align with the first gap.

16. The apparatus according to claim 15, where the first and second gaps each extend approximately 180 degrees plus the fan angle determined by radiation source and detector geometry and distance.

17. The apparatus according to claim 9, where the first device and the second device are the same device or the first device and the second device are movably connected.

18. The apparatus according to claim 9, comprising a second gap in the source path sized to allow a first extremity of the patient to pass through the second gap and a housing for the source path to correspond to the second gap, where the first gap has a circumferential length sufficient to allow the first extremity to pass through the first gap.

19. The apparatus according to claim 9, further comprising a third device configured to adjust the source and detector along the first extremity or to adjust the detector path and source path to a vertical or other angular orientation.

* * * * *